(12) United States Patent
Carre et al.

(10) Patent No.: US 7,473,533 B2
(45) Date of Patent: Jan. 6, 2009

(54) MEMBRANE ARRAYS AND METHODS OF MANUFACTURE

(75) Inventors: Alain R. E. Carre, Le Chatelet-En-Brie (FR); Alexander M. Efremov, St. Petersburg (RU); Ye Fang, Painted Post, NY (US); Yulong Hong, Painted Post, NY (US); Valerie Lacarriere, Larchant (FR); Joydeep Lahiri, Painted Post, NY (US); Fang Lai, Painted Post, NY (US); John C. Mauro, Painted Post, NY (US); Srikanth Raghavan, Ithaca, NY (US); Brian L. Webb, Painted Post, NY (US)

(73) Assignee: Corning Incorporated, Corning, NY (US)

(*) Notice: Subject to any disclaimer, the term of this patent is extended or adjusted under 35 U.S.C. 154(b) by 452 days.

(21) Appl. No.: 11/026,371

(22) Filed: Dec. 30, 2004

(65) Prior Publication Data
US 2006/0147993 A1    Jul. 6, 2006

(51) Int. Cl.
G01N 17/04 (2006.01)
G01N 33/566 (2006.01)
C12Q 1/00 (2006.01)
C07K 14/705 (2006.01)

(52) U.S. Cl. .................. 435/7.2; 205/777.5; 216/2
(58) Field of Classification Search .................. None
See application file for complete search history.

(56) References Cited

U.S. PATENT DOCUMENTS

| | | | | |
|---|---|---|---|---|
| 6,863,833 | B1 * | 3/2005 | Bloom et al. | 216/2 |
| 2002/0019015 | A1 | 2/2002 | Lahiri et al. | 435/7.9 |
| 2002/0094544 | A1 | 7/2002 | Fang et al. | 435/7.9 |
| 2003/0098248 | A1 * | 5/2003 | Vogel et al. | 205/777.5 |

OTHER PUBLICATIONS

Fang et al., "G Protein-Coupled Receptor Microarrays for Drug Discovery", Drug Discovery Today, vol. 8. No. 16, Aug. 2003, pp. 755-761.
Bieri et al., "Micropatterned Immobilization of a G Protein-Coupled Receptor and Direct Detection of G Protein Activation", Nature Biotechnology, vol. 17, Nov. 1999, pp. 1105-1108.
Fang et al., "Membrane Protein Microarrays", Journal Am. Chem. Soc., vol. 124, No. 11, 2002, pp. 2394-2395.
Fang et al., "G-Protein-Coupled Receptor Microarrays", ChemBioChem, 2002, vol. 3, pp. 987-991.
Hennesthal et al., "Pore-Spanning Lipid Bilayers Visualized by Scanning Force Microscopy", Journal Am. Chem. Soc., 2000, vol. 122, pp. 8085-8086.
Cremer et al., "Formation and Spreading of Lipid Bilayers on Planar Glass Supports", J. Phys. Chem. B, 1999, vol. 103, pp. 2554-2559.
Théato et al., "Formation of Lipid Bilayers on a New Amphiphilic Polymer Support", Langmuir, 2000, vol. 16, pp. 1801-1805.
Majewski et al., "Structural Studies of Polymer-Cushioned Lipid Bilayers", Biophysical Journal, vol. 75, Nov. 1998, pp. 2363-2367.
Liu et al., "Fluorescence Enhancement from an Array of Subwavelength Metal Apertures", Optics Letters, vol. 28, No. 7, Apr. 1, 2003, pp. 507-509.
Pierce et al., "Seven-Transmembrane Receptors", Nature Reviews, Molecular Cell Biology, vol. 3, Sep. 2002, pp. 639-650.
Fang et al., "The Growth of Bilayer Defects and the Induction of Interdigitated Domains in the Lipid-Loss Process of Supported Phospholipid Bilayers", Biochimica et Biophysica Acta, 1324. 1997, pp. 309-319.

* cited by examiner

*Primary Examiner*—John D Ulm
(74) *Attorney, Agent, or Firm*—Thomas R. Beall; John L. Haack

(57) ABSTRACT

The invention relates to G protein-coupled receptor (GPCR) microarrays on porous substrates for structural or functional analyses of GPCRs, and methods of preparing porous substrate surfaces for receiving membranes that comprise GPCRs. In one embodiment, a GPCR microarray of the invention comprises a membrane adhered to an upper surface of a porous substrate, the membrane spanning across a plurality of pores on the porous substrate to form a plurality of cavities having sufficient geometry to permit entry of assay reagents into each cavity, thereby allowing access of assay reagents to both sides of GPCR in the membrane.

11 Claims, 9 Drawing Sheets

Pore-spanning configuration

Desirable for functional assay

Pore-coating configuration

Not Desirable for functional assay

MEMBRANE ARRAYS AND METHODS OF MANUFACTURE

BACKGROUND OF THE INVENTION

1. Field of the Invention

The present invention relates to G protein-coupled receptor (GPCR) microarrays on porous substrates for structural or functional analyses of GPCRs, and methods of preparing porous substrate surfaces for receiving membranes that comprise GPCRs.

2. Background of Related Art

GPCRs are the single most important class of drug targets—approximately 50% of current drug targets are membrane bound. Despite the large number of GPCR targets and a wide variety of technologies for screening against GPCRs, no methods were available for screening against multiple GPCRs simultaneously. The GPCR microarray technology has been investigated (Fang et al., "G Protein-coupled Receptor Microarrays for Drug Delivery" *Drug Discovery Today*, Vol. 8, No. 16, August 2003, pp. 755-761; Bieri et al., "Micropatterned Immobiliztion of a G Protein-coupled Receptor and Direct Detection of G Protein Activation," *Nature Biotechnology*, Vol 17, November 1999, pp. 1105-1108; Pierce et al., "Seven-Transmembrane Receptors" *Molecular Cellular Biology*, Vol. 3, September 2002, pp 639-650) and their use has been demonstrated for the multiplexed screening of compounds, see for example U.S. Patent Application Publication Nos. 2002/0019015 and 2002/0094544, the entire disclosures of which are hereby incorporated by reference.

The arrays were obtained on flat "2D" glass slides coated with γ-aminopropylsilane (GAPS) and other materials including epoxypropylsilane. Most assay development has focused on "binding assays" that provide information about how much of a compound is bound to a receptor at a particular concentration; based on this information, the affinity of the compound for the receptor can be obtained.

A large fraction of GPCR screening assays—so-called "functional assays"—are based on determining whether the GPCR gets activated as a result of compound binding. The information can be used to classify compounds as agonists, partial agonists, antagonists or inverse agonists. Moreover, functional assays are essential for investigating "orphan" GPCRs, some of which may turn out to be key drug targets. Orphan GPCRs are those without known ligands, which preclude the use of competition assays employing known labeled ligands. Functional assays can be both cell-based and biochemical in nature; cell-based assays are currently the method of choice for functional assays. Cell based assays include reporter gene assays, β-arrestin and GPCR-GFP translocation assays (i.e., receptor internalization and endosome formation). Methods for monitoring the activation of GPCRs by non-cell based assays are mostly limited to monitoring GTP-GDP exchange at the GPCR associated Gα protein using labeled GTP analogues (e.g., $^{35}$S-GTP γS or Eu-GTP). These functional assays are "homogenous" assays, that is, the receptor and the GTP analogue mixed with or without a compound of interest are in solution over the duration of the assay; these assays are then subject to filtration using a filter microplate so that the labeled GTP can be removed by filtration, and only the bound GTP analog molecules can be quantified and the effect of compound on the binding of GTP analog can be examined which can be used to classify the action of compound on the receptors (i.e., non-binder, or antagonist, or agonist, etc).

Limited success has been encountered with the use of fluorescent-dye labeled GTP-γS for functional assays on 2D GAPS surfaces, although functional assays employing radioactively labeled $^{35}$S-GTPγS have been successfully carried out on these surfaces. However, the relatively poor reproducibility of these functional assays limits their applications of GPCR microarrays for compound screening. Moreover, the use of non-radioactive labels is preferred because of safety issues. Europium-labeled GTP (Eu-GTP) (Perkin Elmer Life Science, Boston, Mass.) has been developed as an alternative to $^{35}$S-labeled-GTP, and has been successfully demonstrated their use in functional assays carried out in solution in combination with filter-plates. Realization of Eu-GTP binding assays for GPCR microarrays on porous substrates would greatly benefit their applications for compound screening.

With regard to the production and use of GPCR microarrays, the G protein coupled receptor (GPCR) microarrays are unique in that they require immobilization of both the protein targets and the lipid membrane in which they are embedded (Fang et al., "Membrane Protein Microarrays," *J. American Chemical Society*, Vol. 124, 2002, pp. 2394-2395; Fang et al., "G-Protein Coupled Receptor Microarrays," *Chembiochem.*, Vol. 3, 2002, pp. 987-991). Moreover, the confined proteins should be in their correctly folded conformations. Different types of surfaces have been proposed that meet these requirements (Hennestal et al., "Pore Spanning Lipid Bilayers Visuallized by Scanning Force Microscopy," *J. American Chemical Society*, Vol. 122, 2000, pp. 8085-8086; Cremer et al., "Formation and Spreading of Lipid Bilayers on Planar Glass Supports," *J. Physical Chemistry B*, Vol. 103, 1999, pp. 2554-2559; Theato et al. "Formation of Lipid Bilayer on a New Amphiphiic Polymer Support," *Langmuir*, Vol. 16, 2000, pp. 1801-1805; Majewski et al., "Structural Studies of Polymer-Cushiond Lipid Bilayers," *J. Biophysical Journal*, Vol. 75, 1998, pp. 2363-2367.

Conventional methods for fabricating solid supported membranes exploit gold-thiol, capping of OH-groups by silanes, and electrostatic interactions. The resulting membranes exhibit limited long-term stability due to the lipid loss into the solution when remained in aqueous solutions (Fang and Yang, "The Growth of Bilayer Defects and the Induction of Interdigitated Domains in the Lipid-Loss Process of Supported Phospholipid Bilayer," *Biochim. Biophys. Acta*, Vol. 1324, 1997, pp. 309-319), but their close proximity to the solid surface (typically 0.2-2 nm) limits lateral lipid mobility. Since a membrane-surface separation of at least 1 to 5 nm (preferably at least 2 to 10 nm) is usually required to preserve the biological functions of the membrane proteins associated with the membranes, several approaches have been employed to extend the membrane surface distance, such as the use of lipids with long hydrophilic spacers, the inclusion of polymer cushions between substrate and membrane, and the use of patterns with varied thiol-components that increase lateral mobility and free volume.

A functional GPCR assay is possible if both GPCR terminals are accessible and bioactive. Suspended membranes have been developed on the basis of membranes spanning the pores of porous alumina substrates (Hennestal et al., supra). When the membrane spans the pores there are no issues with steric congestion on either side of the receptor.

A method has been proposed which makes use of "contact printing" to deposit a binding chemistry, such as a moderately positively charged coating, only onto the top surface of a porous substrate. The contact printing includes impregnating a flat polymer stamp with a solution containing the active molecules and brings it in conformal contact with the porous substrate. This effectively transfers the active molecules only onto the top surface of the substrate.

Further, it is also known to perform functional assays for G-Protein Coupled Receptors (GPCRs) in commercially available 96 well plates using a time-resolved fluorometric assay based on GDP-GTP-Eu-labeled exchange on GPCR. The activation of receptors by agonists is made in solution inside wells. The activation signal is detected on the porous bottom of wells where the activated receptor of the GPCR is retained after filtration (see, for example, the DELFIA GTP-binding kit from Perkin Elmer Inc.).

G-protein coupled receptor (GPCR) microarrays are unique in that they allow immobilizing both the protein targets and the lipid membrane in which they are embedded before activation. One advantage of this technique is to use small amounts of expensive receptors and to study several receptors simultaneously in the same well. However, the confined protein should be in their correctly folded conformations. Different types of surfaces have been proposed that meet these requirements as discussed above.

Therefore, it can be realized that effective GPCR microarrays for use in functional assays, e.g., employing particular GTP analogues, are needed. Additionally, a simple method of selecting the appropriate porous substrate for receiving a membrane, enhancing the immobilization of the membrane on the porous support, as well as a simple method of fixing a membrane on the porous support, are needed.

SUMMARY OF THE INVENTION

The present invention overcomes the problems of forming reliable GPCR microarrays described above by providing GPCR arrays on porous substrates for use in functional assays. Membrane arrays comprising other transmembrane proteins can be similarly prepared.

In one aspect, the present invention provides a membrane array which includes (1) a porous substrate comprising a plurality of pores; and (2) a plurality of membranes adhered to the porous substrate. These membranes comprise transmembrane proteins that are accessible to assay agents from both sides of the membrane. Any type of membrane can be used for the present invention, such as biological membrane (e.g., plasma membrane, nuclear membrane, or cell organelle membrane), reconstituted membrane (e.g., liposome, or other unilaminar or multilaminar amphiphilic molecule complexes), or polymer complexes (e.g., hydrogel). These membranes can be either covalently or non-covalently attached to the porous substrate. The transmembrane proteins can be any protein of interest, such as G protein-coupled receptors (GPCRs), ion channels, receptor kinases, or transporters. In many examples, each transmembrane protein includes a ligand-binding domain located on one side of the membrane and an effector-binding domain located on the other side of the membrane.

In one embodiment, each membrane on a membrane array of the present invention comprises a lipid bilayer, and each membrane at least partially spans across one or more pores in the porous substrate. The surface properties of the porous substrate and these pores satisfy the following set of relations:

$$\gamma_{lw}+\gamma_{ls}+2\gamma_{pw}-2\gamma_{lp}-\gamma_{sw}<0 \text{ and}$$

$$\gamma_{ls}<\gamma_{lw}+\gamma_{sw}$$

wherein,
$\gamma_{lw}$=surface tension of the lipid-assay medium interface;
$\gamma_{ls}$=surface tension of the lipid-substrate interface;
$\gamma_{pw}$=surface tension of the pore-assay medium interface;
$\gamma_{lp}$=surface tension of the lipid-pore interface;
$\gamma_{sw}$=surface tension of the substrate-assay medium interface.

In another embodiment, each membrane on a membrane array of the present invention at least partially spans over two or more pores in the porous substrate to form a plurality of cavities. Each cavity has geometry to permit access of assay reagents into the cavity.

In another aspect of the invention, a process is set forth for creating a bi-functional porous substrate in which the process involves three steps. In the first step, the porous layer is coated by a non-binding chemistry. Then, the top surface of the porous layer is exposed to ultraviolet radiation in the presence of ozone to oxidize or remove the organic coating on the top surface of the porous substrate. Thereafter, another binding chemistry is deposited on the bare top surface to create a bi-functional porous substrate.

Finally, an embodiment of the invention also includes a technique of "contact printing" a GPCR-embedded membrane on a porous substrate in which, preferably, a binding chemistry procedure has been previously performed. The binding chemistry procedure can, for example, providing the upper surface of the porous substrate with a moderately positively charged coating onto the upper surface of a porous substrate. However, other binding chemistry procedures well known in the prior art can equally be employed. The contact printing of the invention includes the steps of impregnating a flat polymer stamp with a solution containing active molecules, and bringing the stamp into conformal contact with the upper surface of the porous substrate to effectively transfer the active molecules onto the top surface of the substrate.

BRIEF DESCRIPTION OF THE DRAWINGS

The invention may be further understood by reference to the drawings, wherein.

DETAILED DESCRIPTION OF THE INVENTION

Figure 1A:
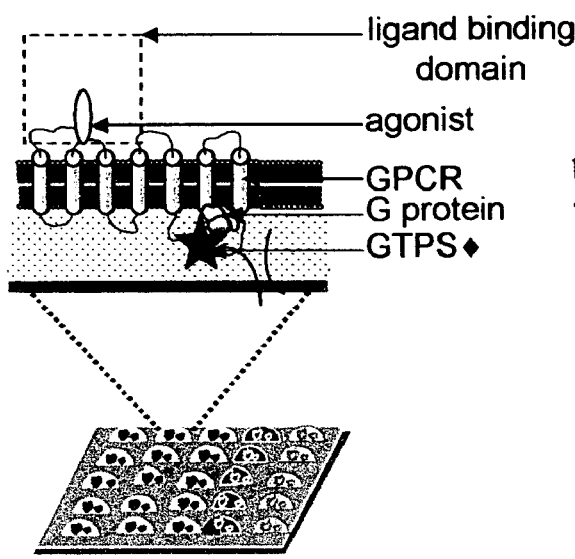
FIGS. 1A and 1B, show an idealized representation of a GPCR microarray on: (A) 2-dimensional substrate and (B) porous substrate.

The invention involves fabrication of GPCR microarrays on porous substrates in order to perform "functional" GPCR assays. It is noted that the ability to carry out functional assays indicates the feasibility of use in binding assays, such as that shown in patent application US 2002/0094544A1, on these porous substrates. Therefore, the instant invention is not limited to providing only functional assays of the GPCR-type, but can be directed to any assay in which exposure of both ends of a protein, across a membrane, is preferred for accurate results. Examples of these proteins include, but are not limited to, ion channels, transporters, kinase receptors, or other transmembrane proteins.

Although conventional protein microarrays provide direct information regarding the binding and selectivity of putative drugs, they fall short in their ability to predict biological function. The biophysical requirements to study ligand agonism or antagonism using microarrays are challenging—a molecule has to bind to an immobilized protein in the microspot, the protein has to then undergo a conformational change that leads to the binding of a second molecule at a different binding site. Yet, two-site tandem binding is the paradigm for the activation of cell-surface receptors.

For binding assays, it is preferred that the ligand binding domain of the GPCR (located on the extracellular N-terminus and/or the extracellular binding sites formed by the membrane spanning loops of the receptor) be exposed to the assay solution (containing the labeled ligand and potential drug compounds). For GPCR containing membrane preparations immobilized on GAPS (or other amine containing surfaces), we assume that 50% of the immobilized receptors have their ligand binding domains facing the solution with the intracellular G-protein binding domain face down on the GAPS surface. GPCRs may also be immobilized in an oriented manner. For example, a GPCR with its ligand binding domain exposed to the solution ("facing up") could be obtained using a GPCR biotinylated (or histidine tagged) at its C-terminus printed on a streptavidin (or N-chelate) coated surface; whereas a GPCR with its G-protein side facing up could be obtained through immobilization via its glycosylated N-terminus on wheat-germ agglutinin-coated surfaces. The latter orientation may be useful if monitoring GPCR-G protein interactions is desired.

For functional assays, access to both sides of the receptor is preferred. In the resting state of the receptor, GDP is bound to the $G_\alpha$ subunit of the heterotrimeric G protein (Gp) associated with the GPCR. Upon activation due to ligand binding, GDP dissociates from the activated complex and is replaced by GTP (or its analogue). Therefore, equilibrium is achieved between the GPCR-Gp complex, the ligand (L), GDP, and the GTP analogue (GTPS♦), as shown in Equations 1 and 2.

$$GPCR\text{-}Gp+L=L\text{-}GPCR^*\text{-}Gp\text{-}GDP \quad (Eq\ 1)$$

$$L\text{-}GPCR^*\text{-}Gp\text{-}GDP+GTPS\blacklozenge=L\text{-}GPCR+Gp\text{-}GTPS\blacklozenge \quad (Eq\ 2)$$

Figure 1B:
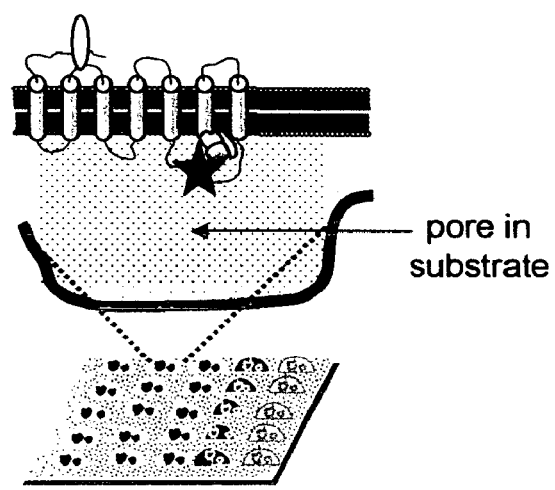

Partitioning of GTPS♦ into the interstitial spaces of a supported membrane can be hindered (FIG. 1A), especially if the label attached to the GTP is bulky. Porous surfaces that lead to the formation of supported membranes spanning the pores (FIG. 1B) of the substrate can alleviate this steric congestion and enable access to both sides of the immobilized receptor. That is, the agonist is able to access the ligand binding domain of the GPCR and GTPS♦ should be able to simultaneously bind to the $G_\alpha$ subunit of Gp (FIG. 1B).

There are additional reasons why porous surfaces are important for functional assays. The increased binding capacity of the surface may lead to the immobilization of a larger number of receptors relative to flat surfaces. Although the binding affinity of a ligand for a GPCR depends on whether it is complexed to a G protein, the overall binding signal is an average signal obtained from complexed and uncomplexed forms (the use of nanaomolar concentrations of ligands biases the assay to the complexed form) of the receptor. Functional assays work for those receptors complexed with right heterotrimeric G-protein. Another advantage in using porous substrates is the potential for optical enhancements due to scattering by the porous microstructure or due to the strong enhancement of the incident light within the nanopores under resonant conditions (Liu, Y. and Blair, "Fluorescence enhancement from an array of subwavelength metal apertures", *Optics Letters*, 2003, Vol. 28, 507). Since the net signal upon functional activation is relatively low, substrates that offer higher sensitivity (assuming that the assay is not limited by non-specific binding) would facilitate the monitoring of GPCR activation.

As discussed further below, the invention describes a process of forming porous surfaces coated with GAPS (or any surface presenting polymers containing amino groups can also be used), the fabrication of GPCR microarrays on these substrates, and functional assays on these arrays that monitor the agonist mediated binding of europium labeled GTP (Eu-GTP) to the microspots form at the pores of the porous substrate.

The process of fabricating and employing the GPCR functional assay of the invention includes three major steps:

1) Array printing—GPCR membranes are printed on GAPS coated porous slides using contact (solid pin or quill pin-based) or non-contact (injet, bubble injet or nanoliter liquid dispenser) printing technologies. Preferably, the printed slides are then subject to post-printing treatments. These treatments include about one-hour incubation under about 75% humidity in a humidity chamber and followed by drying for about two hours under vacuum at room temperature before assay;

2) Assays performing—the printed GPCR arrays are then incubated with assay buffers containing GTP analogue probes in the presence or absence of receptor agonist for certain time (e.g., 45 minutes), and at the end of incubation period the assay solutions are removed, the slides are rinsed with GTP wash buffer and dried with nitrogen;

3) Imaging—when Eu-GTP is used as a probe, the slides are then directly scanned using a time-resolved fluorescence imaging system; and, if biotin-GTPγS is used as a probe, an extra incubation step is often performed before imaging. For example, the array is then further incubated with Gold particles labeled streptavadin in order to detect bounded biotin-GTPγS, resonance light scattering imaging system is then used.

Figure 2:
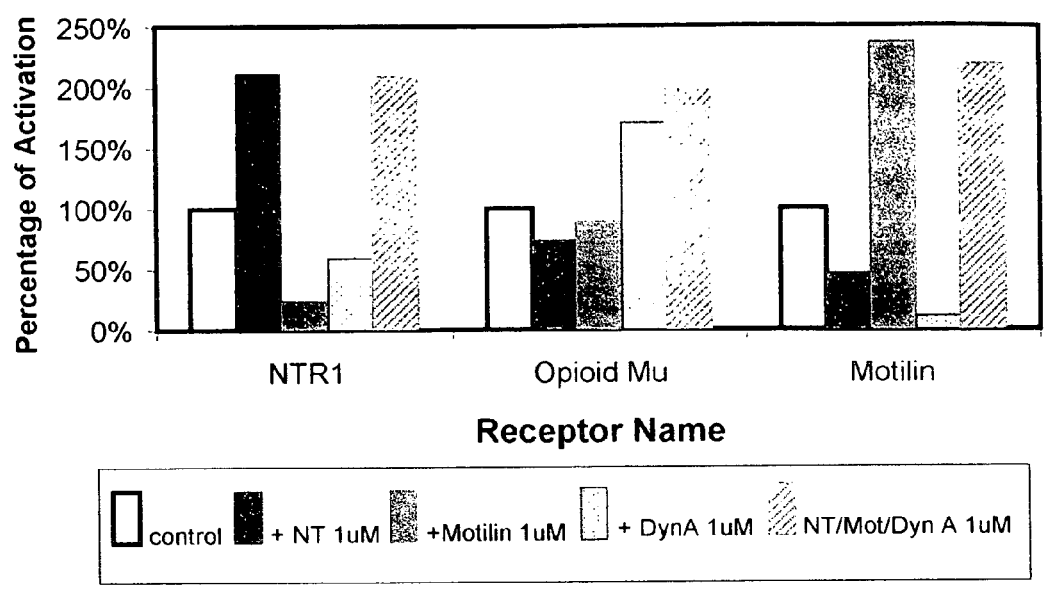
FIG. 2 shows an example of a GPCR array functional assay on GAPS coated porous slide in which human neurotensin receptor subtype 1 (NTR1), opioid receptor mu subtype (Opioid Mu) and motilin receptor (Motilin) were printed in array format on porous slide.

FIG. 2 illustrate an example of a GPCR array functional assay on GAPS coated porous slide of the invention in which NTR1, Opioid Mu and Motilin receptors were printed in array format on porous slide. After two hours of vacuum drying, the arrays were incubated for 1 hour with EuGTP assay buffer in the absence or presence of receptor agonists (neurotensin for NTR1, motilin for Motilin receptor, and dynorphin A for Opioid Mu; each agonist is at 1 μM). The EuGTP assay buffer contained 10 nM Eu-GTP, 50 mM HEPES buffer, pH 7.4, 3 μM GDP, 10 mM $MgCl_2$, 100 mM NaCl, and 0.1% protein blocker. At the end of the incubation, the assay buffers were removed. Afterwards, slides were washed, dried and imaged with in-house developed time-resolved fluorescence imaging system. The degree of activation (%) is plotted for a control and the various receptors. The results suggest that the presence of three agonists (each for its cognate receptor) increase the binding of EuGTP to the GPCR microspots in the arrays, indicating that the GPCRs in the arrays are activated by the agonists.

The use of porous substrates for functional assays using GPCR microarrays of the invention will remove the stringent restrictions on the size of GTP analogues and any other molecules that can recognize or bind specifically to activated receptors (e.g., beta-arrestin) or activated G proteins (e.g., G protein-binding peptides), and thereby provide high quality, high sensitivity functional assays in a highly multiplexed manner.

Additionally, enhanced detection schemes such as those using resonance light scattering (e.g. using GTPγS-biotin, followed by streptavidin coated gold nanospheres) or signal amplification schemes (e.g. using GTPγS-biotin, followed by streptavidin-HRP for amplification) can also be used with the functional assays of the invention. Another embodiment of the invention involves parallel performing binding and functional assays by applying an assay solution containing a GTP analogue as well as labeled ligand(s) with known functional properties (agonist versus antagonist) in the absence or presence of a compound of interest. The GTP analogue gives signals in one channel (e.g., time resolve fluorescence signal of Eu-GTP, or radioactivity signal), whereas the labeled ligands give signals in other channels (e.g., FITC, Cy3 or others). Each labeled ligand binds specifically and selectively to its cognate receptor(s) in the microarrays.

Another embodiment of the invention involves a process of selecting the appropriate porous substrate for use with a particular membrane. In the regard, the invention further includes defining the surface chemistries of the substrate and pore to favor membrane spanning conformations for the GPCR-embedded membranes over an arbitrarily sized pore in the porous substrate. These surface chemistries are based on an analysis of the competition between interfacial energies involving the membrane lipids, substrate, pore, and aqueous environment.

While the focus of this invention is on GPCR array functional assays, it must be realized that the invention is also useful for the immobilization of any bio-layer or membrane (e.g., biological membrane, reconstituted membrane, or polymer such as a hydrogel) when the application requires steric access to both sides of the bio-layer or membrane.

As mentioned above, functional GPCR assays yield far greater information about the effectiveness of drug candidates than binding assays alone, and functional GPCR assays are greatly facilitated by obtaining access to both sides of the GPCR containing membrane. Porous substrates have been identified as candidate surfaces on which a functional GPCR assays can be designed. The present invention enables membrane spanning over arbitrarily sized pores, since the surface designs are to be based on the surface chemistry of interaction. That is, the present invention is independent of the specific coating materials that may be used, and, hence, provides an extremely broad and powerful scope of applications.

Figure 3A:
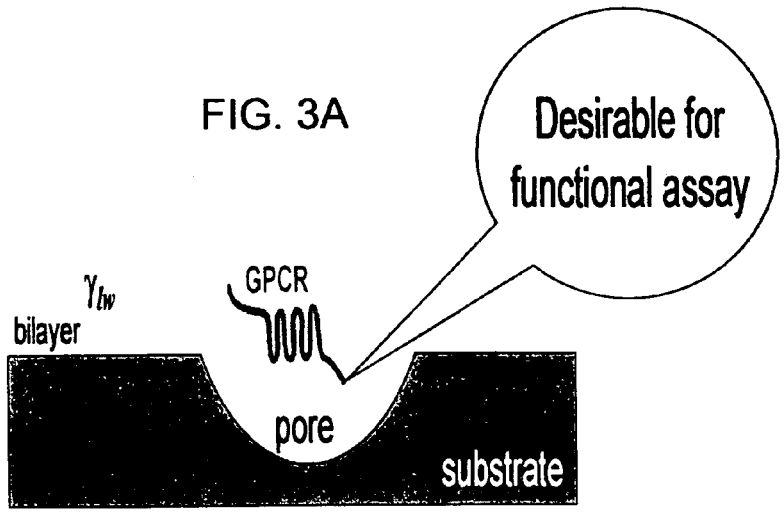
FIGS. 3A and 3B illustrate a pore-spanning configuration (top) in which both GPCR terminals are accessible and bioactive; while, in the pore-coating configuration (bottom), the inner C-terminal is squeezed between the membrane and substrate and, therefore, is not available for functional assay.
Figure 3B:
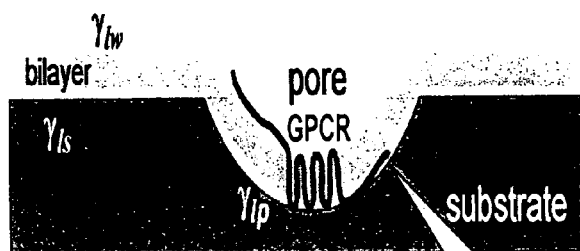

As can be seen in FIGS. 3A and 3B, it is beneficial for the GPCR-receptor to be accessible to the assay medium at both surfaces of the membrane in order to provide reliable binding and results. For substrates with conformal lipid membrane, FIG. 3B, the exposure to the assay medium of the C-terminus end of the GPCR-receptor adjacent the substrate surface is hindered by the close association, e.g., physical contact or squeezing, of the membrane and porous substrate.

Figure 4:
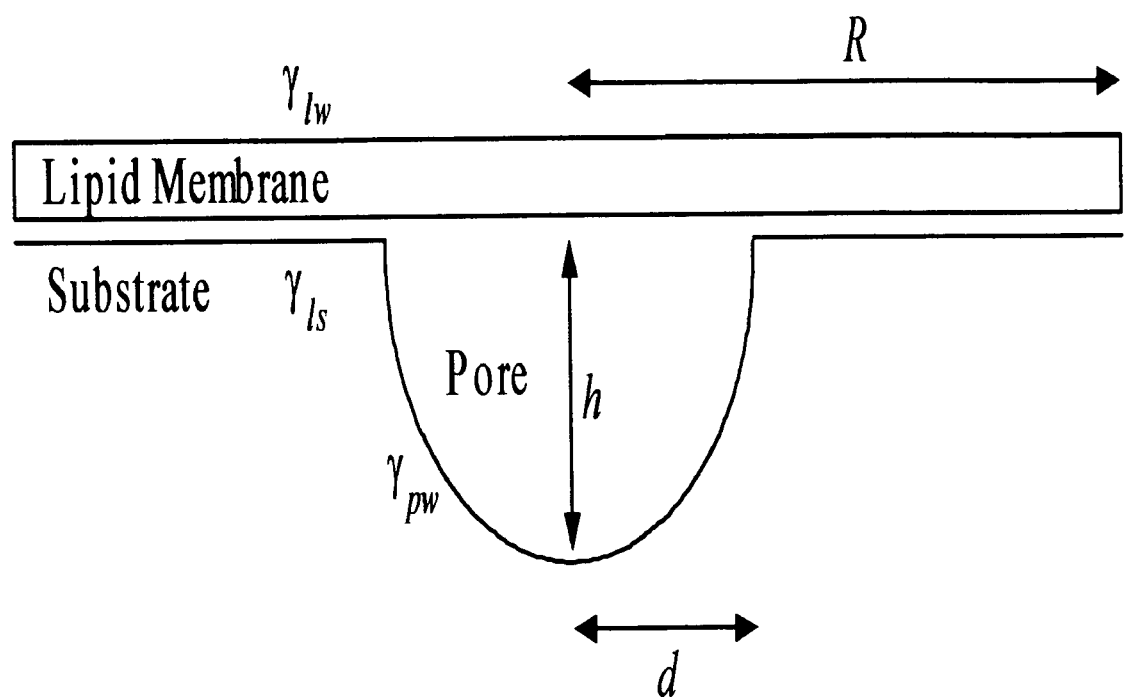
FIG. 4 is a schematic diagram of a pore-spanning membrane desirable for functional assays.
Figure 5:
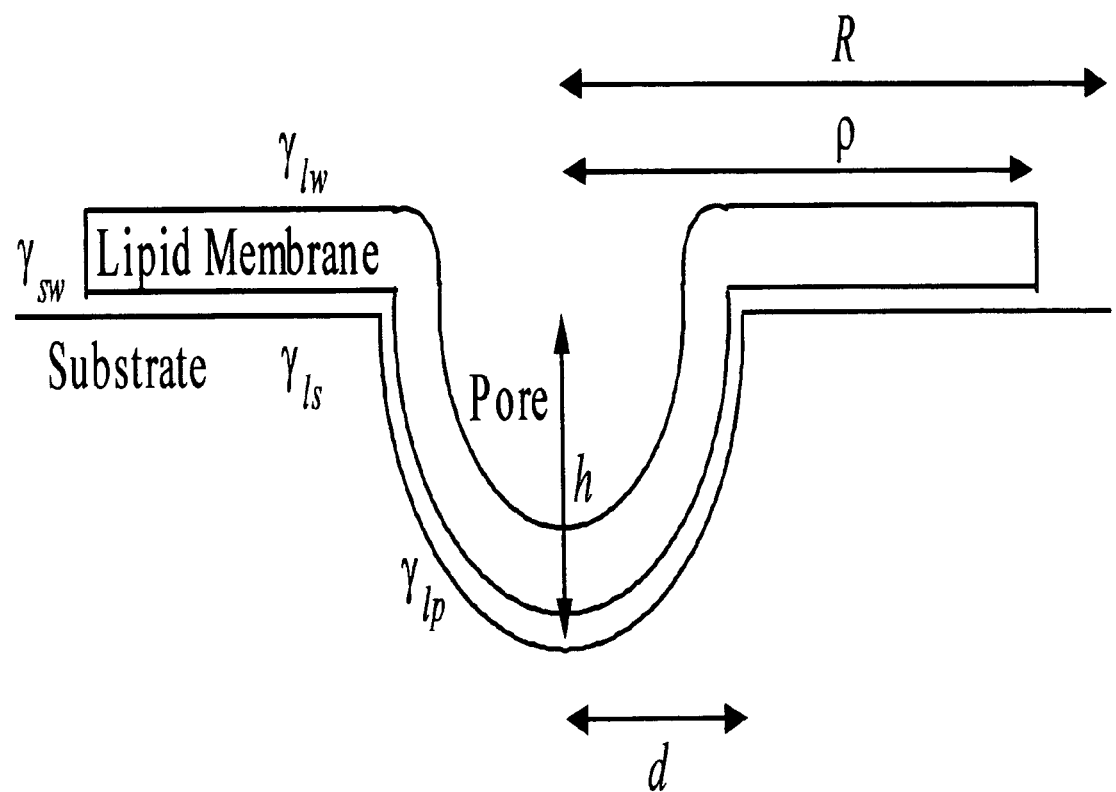
FIG. 5 is a schematic diagram of a pore-coating membrane, which is not desirable for functional assays.

Without limiting the present invention to any particular theory, an analysis of the difference in free energy between the pore-spanning configuration is illustrated in FIG. 4, and the pore-coating configuration is illustrated in FIG. 5, which is given by:

$$\Delta G = \pi d^2(\gamma_{lw} + \gamma_{ls} + 2\gamma_{pw} - 2\gamma_{lp} - \gamma_{sw}) - 4\pi K_c\left(1 + \frac{\pi d}{2t}\right),$$

where:
d=radius of the pore;
$\gamma_{lw}$=surface tension of the lipid-water interface;
$\gamma_{ls}$=surface tension of the lipid-substrate interface;
$\gamma_{pw}$=surface tension of the pore-water interface;
$\gamma_{lp}$=surface tension of the lipid-pore interface;
$\gamma_{sw}$=surface tension of the substrate-water interface;
$K_c$=the bending modulus of the membrane; and
t=the thickness of the membrane.

A negative value of $\Delta G$ indicates that the pore-spanning configuration is favorable; hence, a negative value of $\Delta G$ is desirable for functional assays. If we assume the worst-case scenario for pore-spanning, i.e. a perfectly fluid membrane, we may set $K_c$=0. To allow pore-spanning in this worst-case scenario, we preferably have for a hemispherical pore, $$\pi d^2(\gamma_{lw}+\gamma_{ls}+2\gamma_{pw}-2\gamma_{lp}-\gamma_{sw})<0.$$

Therefore, the ability of a membrane to span a pore can be a function of the surface tension of the substrate and of the pore, and not a function of the pore geometry:

$$\gamma_{lw}+\gamma_{ls}+2\gamma_{pw}-2\gamma_{lp}-\gamma_{sw}<0.$$

If this condition is satisfied, then the pore-spanning membrane configuration is favorable relative to the pore-coating configuration. In many instances, the condition $\gamma_{ls}<\gamma_{lw}+\gamma_{sw}$ is also satisfied to ensure binding of the membrane to the substrate.

Therefore, many embodiments of the present invention are directed to the selection of a porous surface in which the surface chemistries are such that both the conditions $\gamma_{lw}+\gamma_{ls}+2\gamma_{pw}-2\gamma_{lp}-\gamma_{sw}<0$ and $\gamma_{ls}<\gamma_{lw}+\gamma_{sw}$ are satisfied. If the geometry of the pore-shape were generalized, then the first condition above can be generalized to write: $\gamma_{lw}+(S_p/S_d-1)(\gamma_{ls}-\gamma_{sw})-S_p/S_d(\gamma_{lp}-\gamma_{pw})<0$, where $S_p$ refers to the pore surface area and $S_d$ refers to the pore-spanning membrane area of the pore. For instance, for the ideal hemispherical pore, $S_p=2\pi d^2, S_d=\pi d^2$, we obtain the earlier condition.

Therefore, as long as these two inequality conditions are satisfied, the pores may be of any size and geometry suitable for functional assays.

Other hypotheses may also explain why porous substrates enable functional assays for GPCR or other membrane proteins. Biological membranes are unstable on bare (unmodified) flat glass substrates. See, e.g., Cremer et al., supra. Moreover, the use of bare glass substrates do not offset the membrane by a distance (e.g., about 2 nm or less) from the surface that enables the folding of extramembrane domains. However, bare (unmodified) porous glass supports offer mechanical stability and enable specific binding of ligands to GPCR arrays. See, e.g., U.S. patent application entitled "Porous Substrate Plates and the Use Thereof" (by Ye Fang et al., Attorney Docket No. SP04-026). The present invention indicates that these types of supports also enable functional assays. Specifically, the present invention demonstrates that GPCR microarrays on organic polymeric porous supports enable GPCR functional assays. Many theories are available to explain why porous substrates are excellent candidates for functional assays. In addition to the above-described theories, one hypothesis is that porous substrates enable multilayer deposition of membranes in structures such that the tortuosity enforced by the substrate satisfies the requirement for access to both sides of the membrane.

Once the proper selection of porous substrate has been made, it is often necessary to provide the surface of the substrate with the ability to securely receive membranes. One method of providing a bi-functional porous of the invention is to apply a non-binding coating on the entire porous substrate. Then the non-binding coating is oxidized (or burned) at the top surface using an ultraviolet (UV) lamp. The UV lamp, e.g., mercury lamp, emits UV radiation at two different wave lengths, e.g., 185 and 254 nm, to produce ozone and oxidize organic contaminants. Thereafter, a second coating material including silane is grafted on the burned top surface to provide the binding or immobilization sites for GPCR.

This results in a structure in which the top surface of the porous substrate binds to the membrane; while the membrane and GPCR do not bind or adhere to the inner walls of pores which contain the non-binding coating material.

It is known that slightly positively charged surfaces are usually suitable to bind membranes to surfaces. Such surfaces may be obtained by grafting organic groups with amine functions to the substrate surface. If the substrate has a porous layer made from a glass frit, an aminosilane is suitable to modify the glass surface.

The hydrophilic, non-binding properties of the inner pore walls may be obtained if, for example, the untreated glass substrate is hydrophilic or coated with a non-binding coating. Several alternatives can be used. For example, the inner pore walls may be coated with a silane terminated polyethylene glycol (PEG-silane) or with a hydrolyzed epoxy silane.

In a specific method of the invention, the porous substrate is entirely coated by dipping the substrate in a solution containing an organic polymer with a large amount of hydroxyl functions, which provide the non binding properties desired, e.g., a hydrophilic coating is formed. This polymer is prepared by polymerization and hydrolysis, in very acidic conditions (pH=0), of, for example, an epoxysilane (3-Glycidoxypropyltrimethoxysilane, called GLYMO). After 1 minute of dipping, the chemical condensation of the polymer is accelerated by a thermal treatment of 1 hour at 70° C. Then, the excess of polymer not bound onto the substrate is eliminated by rinsing with a water flow for 30 seconds and drying with nitrogen.

Figure 6:
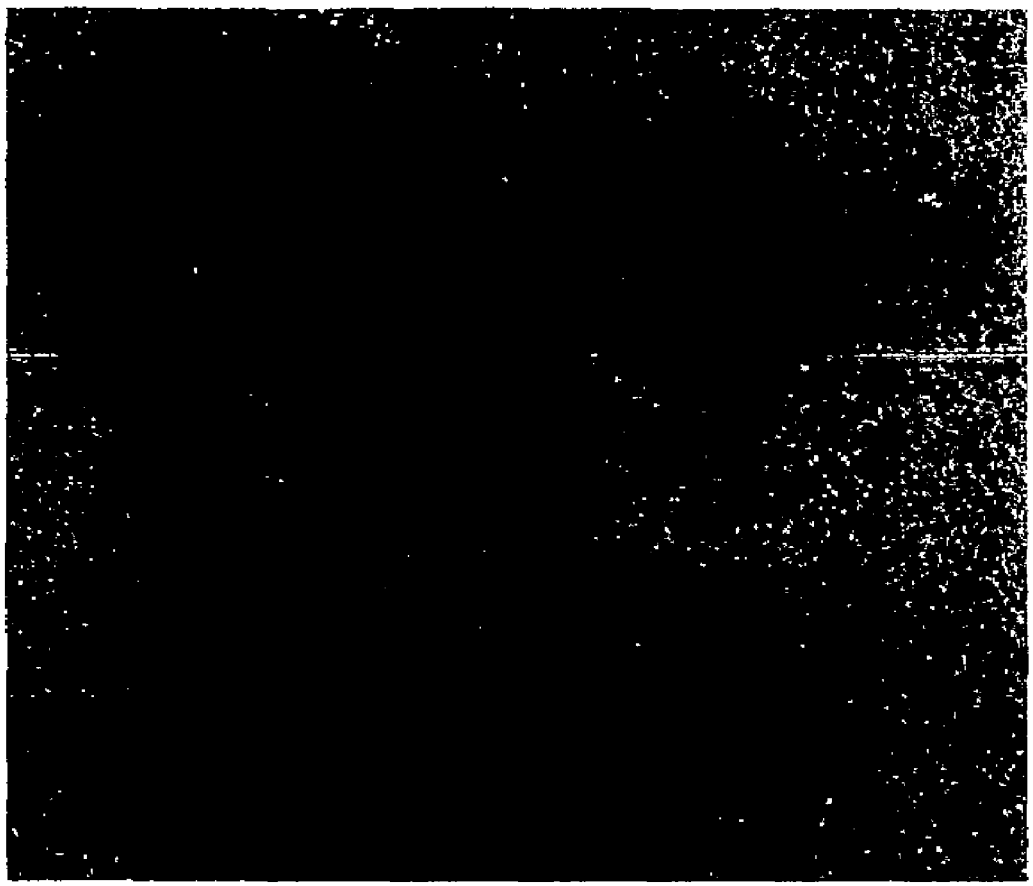
FIG. 6 illustrates a porous substrate untreated with a non-binding compound which has been dipped in Fibrinogen solution and stained with colloidal gold solution.
Figure 7:
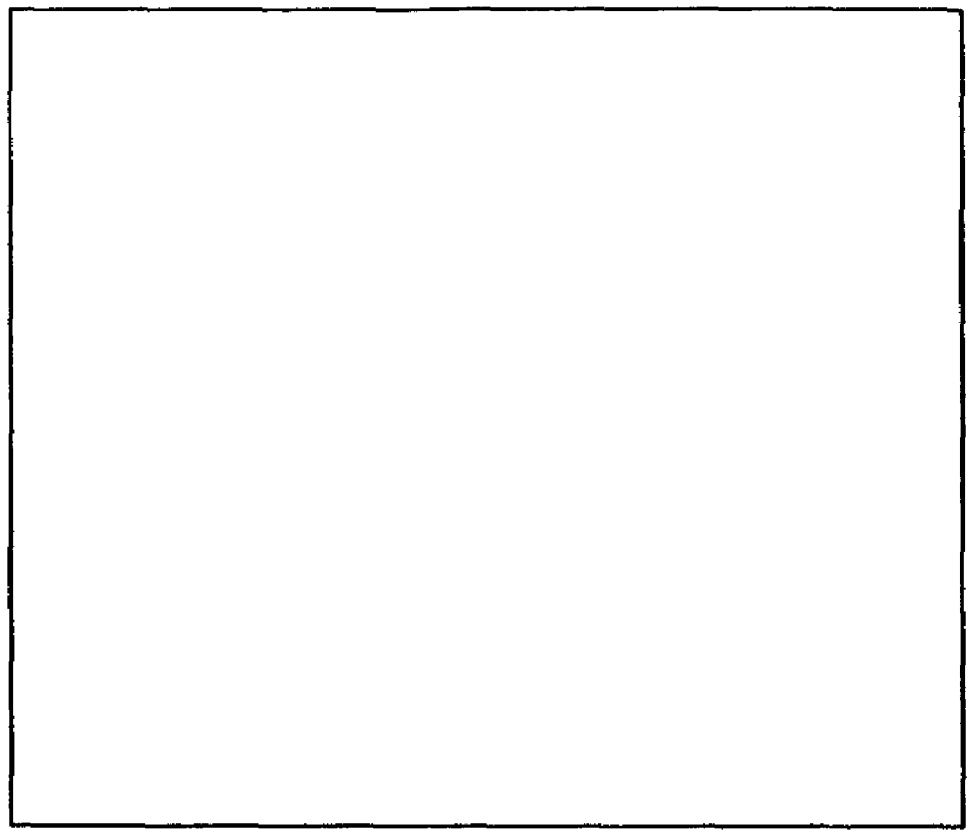
FIG. 7 illustrates a porous substrate treated over its entire surface with a binding compound which has been dipped in Fibrinogen solution and stained with colloidal gold solution.

The non-binding properties of this coating can be checked by dipping the substrate in a fibrinogen aqueous solution (0.1% in PBS). Fibrinogens are proteins, strongly sticking to glass surface and glass frit porous layers. The adsorbed proteins can then be revealed by a colloidal gold staining, as shown in FIGS. 6 and 7, wherein FIG. 6 illustrates the binding of fibrinogen on a clean porous substrate and FIG. 7 illustrates virtually no binding for porous substrate provided with a non-binding compound.

When the non-binding compound coated porous substrate is subjected to an oxidation treatment in the presence of ozone (formed from oxygen exposed to UV at 185 nm which is associated with UV at 254 nm), burning of the non-binding organic compound from the upper surface of the treated substrate results. In many cases, the thickness of the layer to be burned is only a few molecular layers. For example, one hour of exposure of a coated sample under this lamp results in a "cleaned" upper surface, free of organics and presenting reactive SiOH sites.

This surface can be used for direct binding of GPCR or for further functionalization of the top surface, e.g., with silane.

After the burning of the non-binding coating at the top surface of the porous substrate, the 3-aminopropyltriethoxysilane (called GAPS), which provides amine functions for further GPCR-containing membrane immobilization, is applied using a vapor phase (CVD) deposition process. The presence of GAPS silane grafted onto the top surface can be revealed with a colloidal Gold staining.

Figure 8:
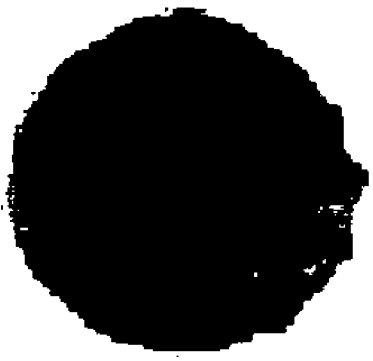
FIG. 8 illustrates a porous substrate, having a GAP coating only on the entire surface, after gold staining.
Figure 8:
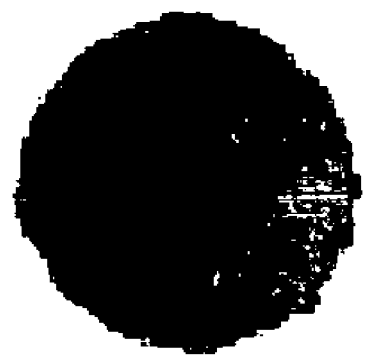
Figure 8:
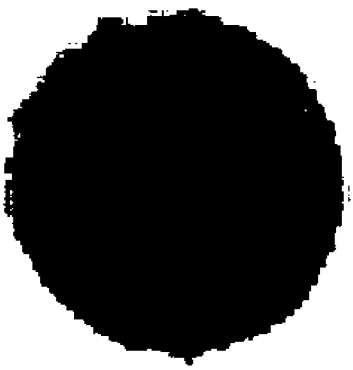
Figure 8:
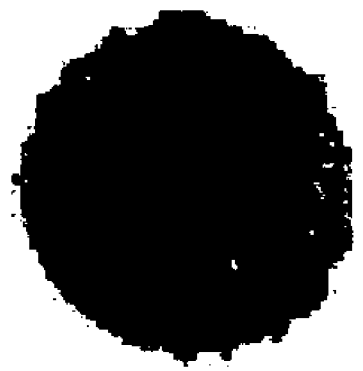
Figure 9:
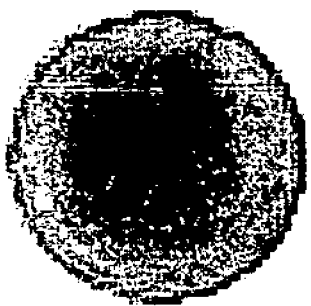
FIG. 9 illustrates a porous substrate of the invention having received a non-binding compound and exposure to ultraviolet radiation in presence of ozone and GAPS coating only on the top surface, after gold staining.
Figure 9:
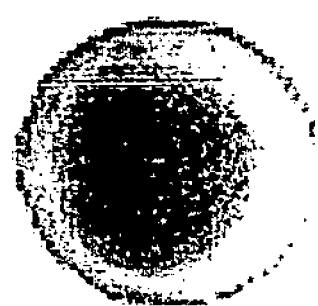
Figure 9:
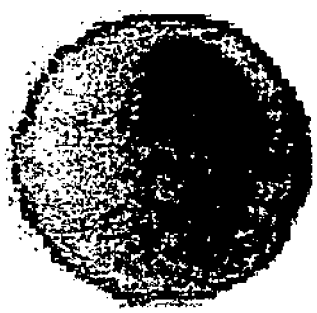
Figure 9:
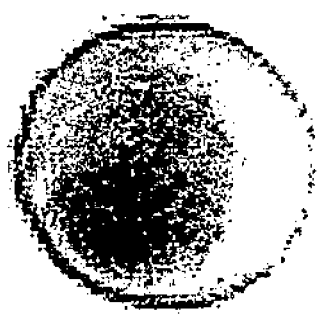

FIGS. 8 and 9 illustrate the results of performing the above invention. That is, the clean porous substrate only coated with GAPS (FIG. 8) presents an intense gold staining on the porous areas; while the bi-functionalized porous substrate of the invention, with a GAPS coating only at the top surface, presents a lighter gold stain. This result is presumed to occur due to a thinner layer of porous substrate being coated with GAPS silane, i.e., the thinner layer corresponding to the thickness of the non-binding coating burned with the UV lamp producing ozone.

Still embodiment of the invention includes providing the porous substrate upper surface with binding capability, e.g., GAPS silane, in order to immobilize membranes thereon.

This result may be obtained when the top surface of the porous substrate binds to the membrane and when the membrane and the GPCR do not bind or adhere to the inner walls of pores.

As mentioned above, slightly positively charged surfaces are usually suitable to binds membranes. Such surfaces may be obtained by grafting organic groups with amine functions to the substrate surface. If the substrate has a porous layer made from a glass frit, an aminosilane is suitable to modify the glass surface. Amine functionality may be also obtained on a glass surface by first grafting an epoxysilane, and then derivatizing the epoxy groups with a diamine or polyamine to form an aminated surface.

The hydrophilic, non-binding properties of the inner pore walls may be obtained if the untreated glass surface is hydrophilic or coated with a non-binding coating, as in FIG. 9. To provide a membrane receptive surface, the application of, for example, functional silanes, on solid surfaces by a dry-printing technique has been described. The process includes impregnating a silicone rubber stamping pad, which bears a mask pattern in relief, with octadecyltrichlorosilane, and then in pressing the pad against a flat surface of silicon or of oxides of metals such as Ti and Al. A reaction takes place between the silane and the coated surface such that the silane molecules are bound to the surface via one of their ends. This surface is then subjected to chemical etching intended to attack the parts which are not protected by the silane mask.

The instant invention provides for a simpler and more effective process of forming the membrane receptive surface on porous substrates which provides a coating of molecular thickness on a three-dimensional, porous substrate by dry or contact printing of a compound having an affinity for the substrate. The transfer element whose impregnated surface is flat and uniformly impregnated is placed in contact with a substrate containing relatively high exposed parts (upper porous surface) and relatively low recessed parts (pores), so as to selectively apply the compound/coating onto the high exposed parts of the substrate, leaving the low recessed parts essentially free of compound.

The dry printing process may typically be carried out by performing the following steps:
(a) providing a transfer element with a flat surface made of a rubbery material capable of undergoing swelling under the effect of an organic solvent;
(b) preparing a solution, in an organic solvent, of a compound having an affinity for the substrate, e.g., capable of bonding to or associating with the substrate surface by any mechanism such as chemical bonding, attraction of opposite electrical charges, or hydrogen bonding;
(c) applying the solution to the clean flat surface of the transfer element, and allowing the transfer element to absorb the solution completely. Evaporation of the solvent may also take place;
(d) pressing the surface of the transfer element treated with the solution against a clean porous substrate and leaving in contact until the molecules of the compound are bonded to the surface of the substrate thereby forming a coating of molecular thickness bonded to the relatively high exposed parts (upper surface) of the porous surface of the substrate; and
(e) separating the transfer element from the substrate.

When the coated compound is an organosilane, it may be one selected from two different types of groups. The first type includes those organosilanes which have a functional group that reacts with groups present on the substrate surface. The second type of functional groups is not reactive with a hydroxyl group, in contrast with the first type.

One class of compounds which can be used in the practice of the invention is those silanes of the general formula $R_n$—Si—$X_{4-n}$, where R is a functional group which is not reactive with a hydroxyl group; X is a group which is reactive, and/or which is hydrolyzable into a group which is reactive, with a hydroxyl group, and n=1, 2 or 3. For example, R may be an epoxy group or a radical containing the epoxy group or an amino group or a radical containing an amino group. X may be, for example, a chlorine atom or an alkoxy group, such as methoxy and ethoxy.

Specific examples of silanes which can be used in the invention include, but are not limited to,
  (3-glycidoxypropyl)trimethoxysilane,
  (3-glycidoxypropyl)methyldimethoxysilane,
  (3-glycidoxypropyl)methyldiethoxysilane,
  (3-glycidoxypropyl)dimethylethoxysilane,
  3-aminopropyltriethoxysilane,
  3-aminopropyltrimethoxysilane,
  4-aminobutyltriethoxysilane,
  N-(2-aminoethyl)-3-aminopropylmethyldimethoxysilane,
  N-(2-aminoethyl)-3-aminopropyltrimethoxysilane,
  N-(6-aminohexyl)aminorpropyltrimethoxysilane,
  3-aminopropyldimethyethoxysilane,
  3-aminopropylmethyldiethoxysilane.

The compound may also be any organic molecules whose groups react with a silane coated substrate. For example, in an alternative to the above-described method for providing a surface for immobilizing the membrane, the porous substrate may be first entirely coated with an epoxysilane, and then the top surface of the porous layer may selectively react with a polyamine deposited by dry printing. This technique is essentially the same as for the selective deposition of any organosilane. However, in the alternative, the organic compound reacts with the epoxy functionality of the silane coated porous layer. As a result, the top surface of the substrate has amine groups and the internal part of the porous layer stays coated by the epoxy silane. In a last step, the epoxy functions can be hydrolyzed as to form a hydrophilic, uncharged, and non-binding surface inside the porosity.

The transfer element can be made of any solid or solid-like material capable of undergoing swelling under the action of an organic solvent. For example, a rubber such as a silicone, polyisoprene, polybutadiene or polychloroprene rubber; butadiene-styrene, butadiene-acrylonitrile, ethylene-propylene or ethylene-vinyl acetate elastomeric copolymers; butyl rubber, and polysulfide rubber. However, a silicone rubber is preferred.

The organic solvent may be any solvent capable of dissolving the compound to be deposited and of exerting a swelling effect on the material of the transfer element. An example of those types of solvents would be liquid alkanes such as hexane, heptane, octane, decane and hexadecane; halogenated alkanes such as chloroform, aromatic compounds such as benzene or toluene; petroleum fractions such as white spirit, diesel oil, gasoline and other solvents such as tetrahydrofuran and N-methylpyrrolidone. Indeed, most organic solvents may be suitable for the invention and a simple routine test will make it possible to check the usefulness of a given solvent. It suffices to impregnate the transfer element with small amounts of compound and, for this, very dilute compound solutions are sufficient.

The porous substrate can be any material whose surface bears hydroxyl groups. An example of those type of substrate would be glass, silica, metals, or polymers whose surface has been modified to create hydroxyl groups thereon, for example by a chemical oxidizing treatment or with a plasma, or alternatively coated with a layer of glass, silica or metal by techniques such as sputtering, chemical deposition in the vapor phase, or sol gel. In many cases, the pore size of the substrate is greater than 0.05 µm.

The compound solution may be applied to the transfer element, or polymer stamping pad, in various ways, for example by rubbing an absorbent paper soaked with the solution onto the transfer element, by rubbing a porous material, such as a sponge, soaked with the solution onto the transfer element, by applying the solution using a doctor blade or an air blade, a sprayer or a coating roller.

This process of the invention may be used to impart adhesion to the relatively high exposed parts (upper surface) of the surface of a porous substrate, containing hydroxyl groups, to a membrane. The inner walls of the porous substrate have to be hydrophilic and uncharged to develop non-binding properties, such as by the process of described for the porous substrate of FIG. 9 above. Clean bare porous glass substrates may be suitable; however, if not, a non-binding chemistry can be deposited or developed inside the porous structure, as described above. Several different options for performing the process of this invention are illustrated by the following examples.

EXAMPLE 1

A porous bi-functional substrate may be obtained from a glass slide coated with a porous layer. The porous layer can be made from a glass frit having the appropriate particle size to form pores having a diameter greater than 0.05 µm, typically of the order of 1 µm after sintering. The top surface of the porous structure is coated by dry printing with aminopropylsilane. Thus the top surface of the substrate becomes slightly positively charged to retain the membrane. The inner part of the porous structure stays as a hydrophilic, hydroxyl rich surface, which may not allows binding of the GPCR protein and membrane inside the pores.

EXAMPLE 2

As an alternative to example 1, after having dry printed the top surface of the porous substrate with an aminosilane, the inner part of the porous structure can be coated with a silane terminated PEG. This non-binding coating will be grafted onto uncoated glass part, e.g., in the inner part of the porous structure.

EXAMPLE 3

A slide coated with a porous layer with a pore size of the order of 1 μm is completely coated with an epoxy silane, such as glycidoxypropyltrimethoxysilane, by liquid or vapor phase deposition. The top surface of the porous structure is selectively derivatized by dry printing a diamine or a polyamine. The diamine may be for example ethylene diamine, tetraethylene pentamine, or hexamethylene diamine. The epoxy functions inside the porous structure can be hydrolyzed in acidic conditions to form a hydrophilic, uncharged and non-binding coating inside the pores.

The foregoing examples of specific compositions, processes, and/or articles employed in the practice of the present invention are of course intended to be illustrative rather than limiting, and it will be apparent that numerous variations and modifications these specific embodiments may be practices within the scope of the appended claims.

What is claimed is:

1. A membrane array comprising:
   a porous substrate comprising a non-porous base region and a porous region adjacent to the non-porous base region and
   a plurality of membranes adhered to the substrate upper surface of the porous region; each membrane comprising a transmembrane protein, the transmembrane protein being accessible to assay agents on both sides of the membrane.

2. The membrane array of claim 1, wherein the transmembrane protein comprises a ligand-binding domain located on one side of the membrane and an effector-binding domain located on the other side of the membrane.

3. The membrane array of claim 2, wherein the transmembrane protein is a G protein-coupled receptor (GPCR).

4. The membrane array of claim 3, wherein the membrane comprises a lipid bilayer, and the porous substrate comprises a nanoporous or microporous material.

5. The membrane array of claim 4, wherein the membrane at least partially spans over one pore, and the surface properties of the porous substrate and one pore satisfy the following set of relations:

$$\gamma_{lw}+\gamma_{ls}+2\gamma_{pw}-2\gamma_{lp}-\gamma_{sw}<0 \text{ and}$$

$$\gamma_{ls}<\gamma_{lw}+\gamma_{sw}$$

wherein,
$\gamma_{lw}$=surface tension of the lipid-assay medium interface;
$\gamma_{ls}$=surface tension of the lipid-substrate interface;
$\gamma_{pw}$=surface tension of the pore-assay medium interface;
$\gamma_{lp}$=surface tension of the lipid-pore interface; and
$\gamma_{sw}$=surface tension of the substrate-assay medium interface.

6. The membrane array of claim 3, wherein the membrane is adhered to an upper surface of the porous substrate such that the membrane at least partially spans over two or more pores to form a plurality of cavities, each cavity being accessible to said assay agents.

7. The membrane array of claim 3, wherein the membrane further binds to a G protein which is capable of interacting with said GPCR upon binding of said GPCR to a GPCR ligand.

8. The membrane array of claim 1, wherein the porous substrate comprises a material selected from the group consisting of glass, silica, metal and polymer, and wherein the porous substrate includes hydroxyl groups or amino groups on a surface thereof, and the membrane is adhered to the outer surface of the porous substrate.

9. The membrane array of claim 1, wherein the membrane is a cellular membrane.

10. The membrane array of claim 1, wherein the transmembrane protein is selected from the group consisting of an ion channel, a kinase receptor, and a transporter.

11. A method for identifying modulators of a membrane protein, comprising:
   contacting a membrane with a candidate molecule, said membrane comprising said membrane protein and being immobilized on a porous substrate of a membrane array as in any one of claims 1-10, and both sides of said membrane being accessible to assay agents; and
   detecting a function of said membrane protein, wherein a change of said function in the presence of said candidate molecule as compared to that in the absence of said candidate molecule is indicative that said candidate molecule is a modulator of said membrane protein.

* * * * *

UNITED STATES PATENT AND TRADEMARK OFFICE
CERTIFICATE OF CORRECTION

PATENT NO. : 7,473,533 B2  
APPLICATION NO. : 11/026371  
DATED : January 6, 2009  
INVENTOR(S) : Alain R. E. Carre et al.

Page 1 of 1

It is certified that error appears in the above-identified patent and that said Letters Patent is hereby corrected as shown below:

| Claim | Col. | Line | Description |
|-------|------|------|-------------|
| 1 | 13 | 36 | Please delete the word "substrate" after the word "the". |

Signed and Sealed this

Seventeenth Day of March, 2009

JOHN DOLL  
*Acting Director of the United States Patent and Trademark Office*